US011439643B2

(12) United States Patent
Reddy

(10) Patent No.: US 11,439,643 B2
(45) Date of Patent: Sep. 13, 2022

(54) COMBINATION THERAPY USING BELINOSTAT AND PRALATREXATE TO TREAT LYMPHOMA

(71) Applicant: Spectrum Pharmaceuticals, Inc., Henderson, NV (US)

(72) Inventor: Guru Reddy, Irvine, CA (US)

(73) Assignee: Acrotech Biopharma Inc., East Windsor, NJ (US)

( * ) Notice: Subject to any disclaimer, the term of this patent is extended or adjusted under 35 U.S.C. 154(b) by 0 days.

(21) Appl. No.: 15/736,550

(22) PCT Filed: Jun. 14, 2016

(86) PCT No.: PCT/US2016/037384
§ 371 (c)(1),
(2) Date: Dec. 14, 2017

(87) PCT Pub. No.: WO2016/205203
PCT Pub. Date: Dec. 22, 2016

(65) Prior Publication Data
US 2018/0177783 A1 Jun. 28, 2018

Related U.S. Application Data

(60) Provisional application No. 62/180,368, filed on Jun. 16, 2015.

(51) Int. Cl.
*A61K 31/519* (2006.01)
*A61K 31/18* (2006.01)
*A61K 31/714* (2006.01)
*A61P 35/00* (2006.01)
*A61K 45/06* (2006.01)

(52) U.S. Cl.
CPC ............ *A61K 31/519* (2013.01); *A61K 31/18* (2013.01); *A61K 31/714* (2013.01); *A61K 45/06* (2013.01); *A61P 35/00* (2018.01)

(58) Field of Classification Search
CPC .... A61K 31/519; A61K 31/18; A61K 31/714; A61P 35/00
See application file for complete search history.

(56) References Cited

U.S. PATENT DOCUMENTS

| 6,028,071 | A | 2/2000 | Sirotnak et al. |
| 6,888,027 | B2 | 5/2005 | Watkins et al. |
| 7,622,470 | B2 | 11/2009 | O'Connor et al. |
| 8,828,392 | B2 | 9/2014 | Lichenstein et al. |
| 8,835,501 | B2 | 9/2014 | Bastin et al. |

FOREIGN PATENT DOCUMENTS

WO WO2014159214 A1 * 10/2014

OTHER PUBLICATIONS

Marchi et al. Clinical Cancer research (2013), vol. 19, pp. 6657-6661 (Year: 2013).*
Lee et al. Clinical Cancer Research (2015), vol. 21. pp. 2666-2670 (Year: 2015).*
Jain et al. (Clin Cancer Res (2015), vol. 21 pp. 2096-2106, pp. 2096-2106) (Year: 2015).*
Dunleavy et al. (Clin Cancer Res (2010), vol. 16, pp. 5608-5617) (Year: 2010).*
O'Connor et al. (J Clin Oncol (2009), vol. 27, pp. 4357-4364) (Year: 2009).*
Beleodaq [online] Retrieved from the internet, Retrieved on Feb. 11, 2019, <url: https://www.accessdata.fda.gov/drugsatfda_docs/label/2014/206256lbl.pdf> (Year: 2014).*
Lee et al. (Clin Cancer Res (2015), vol. 21, pp. 2666-2670) (Year: 2015).*
Zain et al. (Expert Opinion on Pharmacotherapy (2010) vol. 11, pp. 1705-1714) (Year: 2010).*
Chao, et al., Quantitative analysis of dose-effect relationships: the combined effect of multiple drugs or inhibitors, Advances in Enzyme Regulation, 1984, pp. 27-55, vol. 22.
U.S. Department of Health and Human Services Food and Drug Administration, "Guidance for Industry and Reviewers Estimating the Safe Starting Dose in Clinical Trials for Therapeutics in Adult Healthy Volunteers", Dec. 2002, 26 pages, Rockville, MD, USA.
International Search Report for Appln No. PCT/US2016/037384 dated Sep. 1, 2016.
Marchi, et al., Pralatrexate Pharmacology and Clinical Development, Clinical Cancer Research, Dec. 15, 2013, pp. 6659, 6660 and 6661 vol. 19, No. 24.
Zain, et al., Peripheral T Cell Lymphoma: Clinical Utility of Romidepsin, Blood and Lymphatic Cancer: Targets and Therapy, Jun. 13, 2012, vol. 2, pp. 112-114.
Extended European Search Report and Written Opinion for EP Application No. 16812229.9, dated Dec. 12, 2018.
Foss, et al., "A Phase II Trial of Belinostat (PXD101) in Patients with Relapsed or Refractory Peripheral or Cutaneous T-Cell Lymphoma", British Journal of Haematology, vol. 168, No. 6, Mar. 2015, pp. 811-819.
Jain, et al., "Preclinical Pharmacologic Evaluation of Pralatrexate and Romidepsin Confirms Potent Synergy of the Combination in a Murine Model of Human T-Cell Lymphoma", Clinical Cancer Research, Feb. 2015, 1 page.
Lee, et al., "FDA Approval: Belinostat for the Treatment of Patients with Relapsed or Refractory Peripheral T-Cell Lymphoma", Clinical Cancer Research, Mar. 2015, 6 pages.
Reimer, Peter, "New Developments in the Treatment of Peripheral T-Cell Lymphoma—Role of Belinostat", Cancer Management and Research, vol. 7, Jun. 2015, 7 pages.
Zain and O'Connor, "Targeted Treatment and New Agents in Peripheral T-Cell Lymphoma", International Journal of Hematology, vol. 92, No. 1, Jul. 2010, pp. 33-44.
Villar-Garea, et al., "Histone Deacetylase Inhibitors: Understanding a New Wave of Anticancer Agents", Cancer Epigenetics Laboratory, Spanish National Cancer Centre, Madrid, Spain, vol. 112, 2004, pp. 171-178.

(Continued)

*Primary Examiner* — Kortney L. Klinkel
(74) *Attorney, Agent, or Firm* — Lerner, David, Littenberg, Krumholz & Mentlik, LLP

(57) ABSTRACT

The present invention relates to compositions and methods for treating lymphoma in a subject in need thereof, said methods comprising administering to the patient in need thereof a therapeutically effective amount of a combination of belinostat and pralatrexate, wherein said therapeutically effective amount results in a synergistic antiproliferative effect on cancer cell growth.

5 Claims, No Drawings

(56) References Cited

OTHER PUBLICATIONS

Michael Dickinson et al., "Histone Deacetylase Inhibitors: Potential Targets Responsible for Their Anti-Cancer Effect", Invest New Drugs, Dec. 14, 2010, 18 pages.
P.A. Marks et al., "Histone Deacetylase Inhibitors: Potential in Cancer Therapy", Cell Biology Program, Sloan-Kettering Institute, Memorial Sloan-Kettering Cancer Center, Jul. 1, 2009, 17 pages.

* cited by examiner

COMBINATION THERAPY USING BELINOSTAT AND PRALATREXATE TO TREAT LYMPHOMA

CROSS-REFERENCE TO RELATED APPLICATION

The present application is a national phase entry under 35 U.S.C. § 371 of International Patent Application No. PCT/US2016/037384, filed Jun. 14, 2016, which claims the benefit of the filing date of U.S. Provisional Patent Application No. 62/180,368, filed Jun. 16, 2015, all of which is hereby incorporated herein by reference.

FIELD OF THE INVENTION

The present invention relates to methods for treating cancer. More specifically, the present invention relates to methods for treating lymphoma in a patient in need thereof, said methods comprising administering to the patient in need thereof a therapeutically effective amount of a combination of belinostat and pralatrexate, wherein said therapeutically effective amount results in a synergistic antiproliferative effect on cancer cell growth.

BACKGROUND OF THE INVENTION

Despite years of research into the development of new methods of treatment, cancers of the lymphatic system, or lymphomas, remain quite common. For example, more than 60,000 people in the United States are diagnosed with lymphoma each year, including more than 55,000 cases of non-Hodgkin's lymphoma, and these numbers are constantly increasing.

Non-Hodgkins lymphoma (NHL) includes several different types of lymphomas, and are typically classified based on whether the tumors arise from B-lymphocytes ("B-cell lymphomas") or from T-lymphocytes ("T-cell lymphomas"). The former make up the majority of NHLs; only about 15% of NHLs are T-cell lymphomas. The majority of T-cell lymphomas are classified as "peripheral T-cell lymphomas" which arise from mature T-cells. Peripheral T-cell lymphomas include several aggressive subtypes, including, e.g., peripheral T-cell lymphoma not otherwise specified (PTCL-NOS); anaplastic large cell lymphoma (ALCL); angioimmunoblastic T-cell lymphoma (AITL); cutaneous T-cell lymphoma (CTCL) including, e.g., Sezary Syndrome; enteropathy-type T-cell lymphoma; nasal NK/T-cell lymphoma; and hepatosplenic gamma-delta T-cell lymphoma.

The prognosis for those affected by NHL is often poor, as the survival rates for lymphoma patients remain low. Traditional treatments for lymphoma typically depend on the type of lymphoma as well as the medical history of the patient. First-line treatment for many lymphomas typically includes chemotherapy. Such chemotherapy will often entail the administration of a "cocktail" of compounds, e.g., the formulation "CHOP", which includes cyclophosphamide, doxorubicin, vincristine, and prednisone. In addition, certain first-line cancer treatments also include other forms of cancer therapy, such as radiation therapy.

In many cases, patients respond initially to first-line treatments, but subsequently suffer a relapse, i.e., a tumor reappears or resumes growing. Following one such relapse, patients are often treated with further chemotherapy, e.g., with "CHOP" or with other formulations, or, in some cases, the patients are treated with other procedures such as bone marrow transplantation. Again, in many cases, patients initially respond to such additional treatments, but subsequently suffer another relapse. In general, the more relapses a patient suffers, the less agreement there is in the art concerning optimal subsequent treatment. In other cases, a patient fails to respond at all to a treatment, even initially, and is thus said to have a refractory cancer. In such cases as well, little agreement exists in the art regarding optimal subsequent treatment.

Histone deacetylase (HDAC) inhibitors represent a new mechanistic class of anti-cancer therapeutic. Histones are major protein components of chromatin. The regulation of chromatin structure is understood to be a central mechanism for the control of gene expression. As a general paradigm, acetylation of the epsilon amino groups of lysine residues in the amino-terminal tails of nucleosomal histones is associated with transcriptional activation, while deacetylation is associated with condensation of chromatin and transcriptional repression. Acetylation and deacetylation of histones are controlled by the enzymatic activity of histone acetyltransferases (HATs) and histone deacetylases. Several transcription factors including p53 and GATA-1 have also been shown to be substrates for HDACs.

HDAC inhibitors have been shown to enhance histone acetylation and induce the expression of genes associated with cell cycle arrest and tumor suppression. Phenotypic changes induced by HDAC inhibitors include G1, and G2/M cell cycle arrest and apoptosis in tumor cells. While data indicate that HDAC inhibitors can arrest growth of cancer cells by inducing apoptosis, promoting differentiation, inhibiting angiogenesis, and/or sensitizing cancer cells to overcome drug resistance, the exact mechanism(s) by which HDAC inhibitors effectively inhibit cancer cell growth is not clearly understood.

Belinostat (also referred to as PXD-101) is a histone deacetylase inhibitor having the chemical name (2E)-N-hydroxy-3-[3-(phenylsulfamoyl)phenyl]prop-2-enamide. Belinostat received FDA approval for the treatment of patients with relapsed or refractory peripheral T-cell lymphoma in 2014. It is commercially available for injection in the U.S. under the brand name BELEODAQ® (Spectrum Pharmaceuticals, Henderson, Nev.).

In addition to HDAC inhibitors, compounds with antifolate activity can also have therapeutic usefulness as anticancer agents. These agents typically act by inhibiting the activity of dihydrofolate reductase which in turn causes the inhibition of cell division, DNA/RNA synthesis and repair and protein synthesis in rapidly dividing cancer cells. The compound pralatrexate is an antineoplastic folate analog having the chemical name (2S)-2-[[4-[(1RS)-1-[(2, 4-diaminopteridin-6-yl)methyl]but-3ynyl]benzoyl]amino]pentanedioic acid. Pralatrexate is currently FDA-approved for the treatment of relapsed or refractory peripheral T-cell lymphoma. It is commercially available for injection in the U.S. under the brand name FOLOTYN® (Spectrum Pharmaceuticals, Henderson, Nev.)

As evidenced in the recent FDA approvals of new anti-cancer agents such as belinostat and pralatrexate, great strides have been made in the treatment of cancer. Additional treatment paradigms which produce enhanced therapeutic effects, however, are always desirable.

BRIEF SUMMARY OF THE INVENTION

The present invention is based upon the unexpected and surprising discovery that the known HDAC inhibitor, belinostat and the antifolate chemotherapeutic agent pralatrexate when used in combination provide unexpectedly greater efficacy than when the anticancer agents are used alone, and specifically, produce synergistic growth inhibitory effects on certain B-cell lymphoma and T-cell lymphoma cell lines.

Thus, in one aspect, the present invention relates to a method for the treatment of a lymphoma in a patient in need thereof comprising administering to said patient a dosage amount of belinostat and a dosage amount of pralatrexate, wherein the administered amount together comprise a therapeutically effective amount capable of producing a synergistic growth inhibitory effect on the lymphoma. In one embodiment, the lymphoma is a B-cell lymphoma. In a particular embodiment, the B-cell lymphoma is mantle cell lymphoma or diffuse large B-cell lymphoma. In another embodiment, the lymphoma is a T-cell lymphoma. In a particular embodiment, the T-cell lymphoma is a peripheral T-cell lymphoma. In various embodiments, the peripheral T-cell lymphoma is selected from the group consisting of peripheral T-cell lymphoma not otherwise specified (PTCL-NOS); anaplastic large cell lymphoma (ALCL); angioimmunoblastic T-cell lymphoma (AITL); cutaneous T-cell lymphoma (CTCL) including, e.g., Sezary Syndrome; enteropathy-type T-cell lymphoma; nasal NK/T-cell lymphoma; and hepatosplenic gamma-delta T-cell lymphoma.

In another aspect, the invention relates to a pharmaceutical composition comprising belinostat and pralatrexate, and a pharmaceutical carrier or excipient, wherein said composition exhibits a synergistic growth inhibitory effect when used in the treatment of lymphoma.

In another aspect, the present invention pertains to use of belinostat and pralatrexate in the manufacture of a medicament for the treatment of lymphoma wherein said treatment comprises treatment with a dosage amount of belinostat and a dosage amount of pralatrexate, wherein the administered amount together comprise a therapeutically effective amount capable of producing a synergistic growth inhibitory effect on the lymphoma. In one embodiment, the lymphoma is a B-cell lymphoma. In a particular embodiment, the B-cell lymphoma is mantle cell lymphoma or diffuse large B-cell lymphoma. In another embodiment, the lymphoma is a T-cell lymphoma. In a particular embodiment, the T-cell lymphoma is a peripheral T-cell lymphoma. In various embodiments, the peripheral T-cell lymphoma is selected from the group consisting of peripheral T-cell lymphoma not otherwise specified (PTCL-NOS); anaplastic large cell lymphoma (ALCL); angioimmunoblastic T-cell lymphoma (AITL); cutaneous T-cell lymphoma (CTCL) including, e.g., Sezary Syndrome; enteropathy-type T-cell lymphoma; nasal NK/T-cell lymphoma; and hepatosplenic gamma-delta T-cell lymphoma.

DETAILED DESCRIPTION

While the specification concludes with the claims particularly pointing and distinctly claiming the invention, it is believed that the present invention will be better understood from the following description.

Any percentages and ratios used herein are by weight of the total composition unless otherwise indicated herein. All measurements made are at 25° C. and normal pressure unless otherwise designated. All temperatures are in Degrees Celsius unless specified otherwise. The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise.

All ranges recited herein include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

Unless otherwise indicated, as used herein, "a" and "an" include the plural, such that, e.g., "a chemotherapeutic agent" can mean at least one chemotherapeutic agent, as well as a plurality of chemotherapeutic agents, i.e., more than one chemotherapeutic agent, including but not limited to, chemotherapeutic agents of different types.

Where used herein, the term "and/or" when used in a list of two or more items means that any one of the listed characteristics can be present, or any combination of two or more of the listed characteristics can be present. For example, if a composition is described as comprising agents A, B, and/or C, the composition can comprise A feature alone; B alone; C alone; A and B in combination; A and C in combination; B and C in combination; or A, B, and C in combination.

All references cited herein are hereby incorporated by reference in the entirety.

The present invention relates to methods and compositions for the treatment of cancer. Specifically, it has been surprisingly discovered that the combination of belinostat and pralatrexate can have different growth inhibitory effects on different lymphoma cells in vitro. Notably, at certain concentrations, the combination produces additive growth inhibitory results in certain cancer cells; however, in other cancer cells, unexpected synergistic growth inhibitory effects are observed.

In view of these data, it is contemplated herein that patients suffering from certain B or T cell lymphomas may receive a clinical benefit when administered a therapeutically effective amount of a combination of belinostat and pralatrexate. In some cases, the patient may benefit from a therapeutic effect which is additive. In other lymphoma patients, however, the therapeutic effects achieved as a result of the combination treatment may be enhanced or synergistic; i.e., better than additive therapeutic effects.

As used herein, "belinostat" refers to the compound (also known as PXD-101) having the chemical name (2E)-N-hydroxy-3-[3-(phenylsulfamoyl)phenyl]prop-2-enamide. This chemotherapeutic agent is currently commercially available for injection in the U.S. under the brand name BELEODAQ® (Spectrum Pharmaceuticals, Henderson, Nev.). As used herein, the term "belinostat" encompasses the compounds disclosed and claimed in U.S. Pat. Nos. 6,888,027, and 8,835,501 the contents of which are hereby incorporated by reference in their entirety.

In addition, as used herein, "pralatrexate" refers to the compound having the chemical name (2 S)-2-[[4-[(1RS)-1-[(2, 4-diaminopteridin-6-yl)methyl]but-3ynyl]benzoyl]amino]pentanedioic acid. It is currently commercially available for injection in the U.S. under the brand name FOLOTYN® (Spectrum Pharmaceuticals, Henderson, Nev.) As used herein, the term "pralatrexate" encompasses the compounds disclosed and claimed in U.S. Pat. Nos. 6,028, 071 and 7,622,470 the contents of which are hereby incorporated by reference in their entirety.

As contemplated herein, the methods and compositions of the instant invention include use of the indicated chemotherapeutic agents, as well as any pharmaceutically acceptable salts, stereoisomers, solvates, prodrugs, homologs, and analogs thereof.

As used herein, the terms "treatment of cancer", "cancer treatment" and like terms refer to partially or totally inhibiting, delaying, or preventing the progression of cancer, including cancer metastasis; inhibiting, delaying, or preventing the recurrence of cancer, including cancer metastasis; or preventing the onset or development of cancer (chemoprevention) in a mammal, for example a human. The means by which such treatment is achieved is not intended to be limited to any particular biological pathway or mechanism of action.

The methods of treatment of the present invention comprise administering to a patient in need thereof a dosage amount of belinostat and a dosage amount of pralatrexate. These two amounts together comprise a therapeutically effective amount. As used herein, the term "therapeutically effective amount" refers to the combined dosage amount of belinostat and pralatrexate administered in a combination therapy. The combined dosage amount will achieve the desired biological response. In the present invention, the desired biological response is treatment of cancer, i.e., partial or total inhibition, delay, or prevention of the progression of cancer, including cancer metastasis; inhibition, delay, or prevention of the recurrence of cancer, including cancer metastasis; or the prevention of the onset or development of cancer (chemoprevention) in a mammal, for example a human.

As used herein, the terms "chemotherapeutic agent", "pharmaceutically acceptable agents", "active agent" and like terms are meant to include the indicated agent as well as pharmaceutically acceptable salts, stereoisomers, solvates, prodrugs, homologs, and analogs thereof.

As contemplated herein, the combination therapy of the present invention is particularly suitable for use in the treatment of lymphoma, including non-Hodgkin's lymphomas (NHLs). These cancers are familiar to one of skill in the art and include B-cell lymphomas and T-cell lymphomas. Examples of the former include, e.g., mantle cell lymphoma, and diffuse large B-cell lymphoma. Examples of the latter include, but are not limited to, peripheral T-cell lymphoma and subtypes thereof. These subtypes include, e.g., peripheral T-cell lymphoma not otherwise specified (PTCL-NOS); anaplastic large cell lymphoma (ALCL); angioimmunoblastic T-cell lymphoma (AITL); cutaneous T-cell lymphoma (CTCL) including, e.g., Sezary Syndrome; enteropathy-type T-cell lymphoma; nasal NK/T-cell lymphoma; and hepatosplenic gamma-delta T-cell lymphoma.

The terms "patient", "patient in need thereof", "subject in need thereof" and any like terms used herein refer to the recipient of the disclosed cancer treatment. Mammalian and non-mammalian patients are included. In one embodiment, the patient is a mammal. In one embodiment, the patient is a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), caprine (e.g., a goat), a primate, simian (e.g., a monkey or ape), a monkey (e.g., marmoset, baboon), an ape (e.g., gorilla, chimpanzee, orangutan, gibbon), or a human. In one embodiment, the patient is human, canine, feline, murine, bovine, ovine, porcine, or caprine.

In one embodiment, the patient is a human.

As used herein, "synergy" and "synergistic effect" can refer to any substantial enhancement, in a composition of at least two components, of a measurable effect, when compared with the effect of a component of the composition, e.g., one active compound alone, or the complete blend of compounds minus at least one compound. Synergy is a specific feature of a composition including multiple components, and is above any background level of enhancement that would be due solely to, e.g., additive effects of any random combination of components. Thus, as used herein, the term "synergistic growth inhibitory effect" encompasses a demonstrated reduction in cancer cell growth due to the administration of the combination of belinostat and pralatrexate which is greater than an additive effect.

As contemplated herein, an observed growth inhibitory effect is not limited to any particular mechanism of action, and may include, e.g. reduction in cell proliferation and/or an increase in apoptosis, or other means by which tumor cell growth is reduced.

It is contemplated herein that the combination of belinostat and pralatrexate may be administered to a patient as disclosed herein in combination with one or more additional pharmaceutically acceptable agents familiar to one of skill in the art, including but not limited to additional chemotherapeutic agents, which may produce an additional clinical benefit to the patient.

Other useful pharmaceutically acceptable agents that may be administered to a patient in accordance with the methods of the instant invention include, e.g., vitamins or other supplements which may provide a clinical benefit to the patient familiar to one of skill in the art. For example, as understood by one of skill in the art, a patient administered an anti-folate agent such as pralatrexate may clinically benefit from co-administration of vitamin B12 and/or folic acid, or derivatives thereof, e.g., tetrahydrofolate. For example, according to the USFDA, prior to initiating FOLOTYN®, patients should be supplemented with vitamin B12 1 mg intramuscularly every 8-10 weeks and folic acid 1.0-1.25 mg orally on a daily basis.

As understood herein, the use of stereoisomers, prodrugs, homologs, and analogs of the chemotherapeutic and additional pharmaceutically acceptable agents disclosed herein is encompassed by the scope of the instant invention. Such substances are familiar to one of skill in the art.

Suitable pharmaceutically acceptable salts of the active chemotherapeutic agents described herein for use in the methods of the invention include conventional non-toxic salts. As understood by one of skill in the art, these can include a salt with a base or an acid addition salt such as a salt with an inorganic base, for example, an alkali metal salt (e.g., lithium salt, sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, methanesulfonate, benzenesulfonate, p-toluenesulfonate, etc.); a salt with a basic or acidic amino acid (e.g., arginine, aspartic acid, glutamic acid, etc.); and the like.

Dosage Forms and Modes of Administration

Pharmaceutical compositions and formulations comprising belinostat and/or pralatrexate, alone or in combination with one or more additional pharmaceutically acceptable active agent, for use in the methods of the present invention may be produced by one of skill in the art using conventional methods, e.g., as described in Remington's Pharmaceutical Science Handbook, 22$^{nd}$ Edition, Mack Pub. N.Y. 2012. As understood by one of skill in the art, along with the active chemotherapeutic ingredients and optional additional pharmaceuticallyl acceptable active agent(s), it is contemplated herein that the compositions according to the present invention may contain at least one pharmaceutically acceptable vehicle or excipient. These can include, e.g., formulation coadjuvants, e.g. solubilising agents, dispersing agents, suspension agents, and emulsifying agents. The active agents can be administered as active ingredients in admixture with suitable pharmaceutical diluents, excipients or carriers (collectively referred to herein as "carrier" materials) suitably selected with respect to the intended form of administration, that is, oral tablets, capsules, elixers, syrups, and the like, and consistent with conventional pharmaceutical practices.

According to the administration route chosen, the compositions of the instant invention may be in any suitable dosage form(s) appropriate for the agent(s), including, e.g., solid or liquid forms suitable for oral, parenteral or topical administration. For example, oral dosage forms may include dosage forms such as tablets, capsules (which may include sustained release or timed release formulations), pills, powders, granules, elixers, tinctures, suspensions, syrups, and emulsions. For oral administration in the form of a tablet or capsule, one or more of the active agents can be combined with an oral, non-toxic, pharmaceutically acceptable, inert carrier such as lactose, starch, sucrose, glucose, methyl cellulose, microcrystalline cellulose, sodium croscarmellose, magnesium stearate, dicalcium phosphate, calcium sulfate, mannitol, sorbitol, and the like or a combination thereof. Delayed release combination dosage forms, e.g., which can deliver both belinostat and pralatrexate in vivo but at different desired times after administration are contemplated herein, and may be manufactured according to conventional methods using pharmaceutical excipients familiar to one of skill in the art.

For oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn-sweeteners, natural and synthetic gums such as acacia, tragacanth, or sodium alginate, carboxymethylcellulose, microcrystalline cellulose, sodium croscarmellose, polyethylene glycol, waxes and the like. Lubricants that may be used in these dosage forms include sodium oleate, sodium stearate, magnesium stearate, sodium benzoate, sodium acetate, sodium chloride, and the like. Disintegrators include, without limitation, starch methyl cellulose, agar, bentonite, xanthan gum, and the like.

Likewise, the active agents can be administered in intravenous (bolus or infusion), intraperitoneal, subcutaneous, or intramuscular forms, in a manner well known to those of ordinary skill in the pharmaceutical arts. For example, buffers suitable for intravenous administration include glucuronic acid, L-lactic acid, acetic acid, citric acid, or any pharmaceutically acceptable acid/conjugate base with reasonable buffering capacity in the pH range acceptable for intravenous administration of belinostat and/or pralatrexate. Sodium chloride solution wherein the pH has been adjusted to the desired range with either acid or base, for example, hydrochloric acid or sodium hydroxide, can also be employed. Typically, a pH range for the intravenous formulation can be in the range of from about 5 to about 12. In general, a pH range for an intravenous formulation of belinostat, i.e., an HDAC inhibitor having a hydroxamic acid moiety, is about pH 9 to about pH 12. In general, a pH range for an intravenous formulation of pralatrexate is about pH 7.5 to about pH 8.5. The pH of an intravenous formulation comprising both belinostat and pralatrexate may be adjusted accordingly by one of skill in the art using conventional methods.

It is further contemplated herein that active agents for use according to the methods of the instant invention may be suitable for administration in the form of a depot injection or implant preparation which can be formulated in such a manner as to permit a sustained release of one or more of the active ingredients. The active agents can be compressed into pellets or small cylinders and implanted subcutaneously or intramuscularly as depot injections or implants. Implants can employ inert materials such as biodegradable polymers or synthetic silicones, for example, SILASTIC® silicone rubber, or other polymers, e.g., manufactured by the Dow-Corning Corporation.

As understood by one of skill in the art, an anti-cancer agent and/or other pharmaceutically active agent can also be administered to a patient using liposome delivery systems, such as small unilamellar vesicles, large unilamellar vesicles and multilamellar vesicles. Liposomes can be formed from a variety of phospholipids, such as cholesterol, stearylamine, or phosphatidylcholines.

In addition, therapeutically useful active agents can also be delivered using monoclonal antibodies as individual carriers to which the compound molecules are coupled according to conventional methods.

Active pharmaceutical agents can also be prepared with soluble polymers as targetable drug carriers according to conventional methods. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the active agents can be prepared with biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and cross linked or amphipathic block copolymers of hydrogels.

Subcutaneous formulations, e.g., prepared according to procedures well known in the art at a pH in the range between about 5 and about 12, also include suitable buffers and isotonicity agents. They can be formulated to deliver a daily dose of an active agent in one or more daily subcutaneous administrations, e.g., one, two, or three times each day. The choice of appropriate buffer and pH of a formulation, depending on solubility of the active agent to be administered, is readily made by a person having ordinary skill in the art. Sodium chloride solution wherein the pH has been adjusted to the desired range with either acid or base, for example, hydrochloric acid, or sodium hydroxide, can also be employed in the subcutaneous formulation. Typically, a pH range for a subcutaneous formulation can be in the range of from about 5 to about 12. A pH range for a subcutaneous formulation wherein the HDAC inhibitor is belinostat (i.e., having a hydroxamic acid moiety) can be about pH 9 to about pH 12. In general, a pH range for a subcutaneous formulation of pralatrexate is about pH 7.5 to about pH 8.5.

Active agents can also be administered to a patient in intranasal form via topical use of suitable intranasal vehicles. Transdermal delivery, e.g., using skin patches well known to those of ordinary skill in that art, can be used to provide a continuous delivery of active agent throughout a dosage regimen.

Dosage Regimens and Dosage Amounts

As understood by one of skill in the art, a dosage regimen is the modality of drug administration that is chosen to reach a desired therapeutic objective. As contemplated herein, suitable dosage regimens utilizing the combination of active agents described herein can be selected in accordance with a variety of factors including, e.g., the type, species, age, weight, and sex of the patient; the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug(s) required to treat, for example, to prevent, inhibit (fully or partially) or arrest the progress of the disease.

The dosage amounts of the disclosed anti-cancer agents as well as any optional additional pharmaceutical agents to be administered according to the methods of the instant invention can be determined by a physician or other skilled professional according to conventional methods and based on the relevant circumstances, including the condition to be treated, the chosen route of administration, the actual compounds administered, drug combination, the age, body weight, and response of the individual patient, the severity of the patient's symptoms, and the like. For any compound, the therapeutically effective dose can be estimated initially either in cell culture assays or in animal models, usually mice, rats, guinea pigs, rabbits, dogs, or pigs. The animal model may also be used to determine the appropriate concentration range and route of administration. Such information can then be used to determine useful doses and routes for administration in humans. In calculating the Human Equivalent Dose (HED) it is recommended to use the conversion table provided in Guidance for Industry and Reviewers document (2002, U.S. Food and Drug Administration, Rockville, Md., USA), Generally, an effective dose of a chemotherapeutic agent will be from 0.01 mg/kg to 2000 mg/kg of pharmaceutical agents, preferably from 0.05 mg/kg to 500 mg/kg of pharmaceutical agent. The precise effective dose for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. As understood by one of skill in the art, the dosage amount of any pharmaceutical agent administered according to the methods of the present invention should not exceed the maximum tolerated dose of the agent.

For example, as understood by one of skill in the art, oral dosages of anti-cancer agents for use with the methods of the instant invention can range between about 2 mg to about 2000 mg per day, such as from about 20 mg to about 2000 mg per day, such as from about 200 mg to about 2000 mg per day. For example, oral dosages can be about 2, about 20, about 200, about 400, about 800, about 1200, about 1600 or about 2000 mg per day. It is understood that the total amount per day can be administered in a single dose or can be administered in multiple dosing such as twice, three or four times per day.

For example, a patient can receive between about 2 mg/day to about 2000 mg/day, for example, from about 20 to 2000 mg/day, such as from about 200 to about 2000 mg/day, for example from about 400 mg/day to about 1200 mg/day of an active agent. A suitably prepared medicament for once a day administration can thus contain between about 2 mg and about 2000 mg, such as from about 20 mg to about 2000 mg, such as from about 200 mg to about 1200 mg, such as from about 400 mg/day to about 1200 mg/day. The active agents can be administered in a single dose or in divided doses of two, three, or four times daily. For administration twice a day, a suitably prepared medicament would therefore contain half of the needed daily dose.

With regard to the treatment patients with relapsed or refractory peripheral T-cell lymphoma, the FDA recommended dose and schedule for belinostat is 1,000 mg/m$^2$ BELEODAQ® administered over 30 minutes by intravenous infusion once daily on days 1-5 every 3 weeks. With regard to pralatrexate, the FDA recommended dose of FOLOTYN is 30 mg/m$^2$ administered as an intravenous push over 3 to 5 minutes once weekly for 6 weeks in 7-week cycles.

As understood herein, the dosage amounts of belinostat and pralatrexate to be administered in combination according to the methods of the instant invention is such that the combination produces a therapeutically effective amount capable of producing synergistic growth inhibitory effects on a lymphoma. As discussed above, such amount can vary by subject depending on a variety of factors, including the lymphoma to be treated, and the condition of the patient.

For example, as contemplated herein, intravenously or subcutaneously, the patient can receive belinostat in quantities sufficient to deliver between about 3 to 1500 mg/m$^2$ per day, for example, about 3, 30, 60, 90, 180, 250, 300, 600, 900, 1200 or 1500 mg/m$^2$ per day. In a particular embodiment, the patient can receive belinostat in quantities sufficient to deliver between about 250 to about 1000 mg/m$^2$ per day. Such quantities can be administered in a number of suitable ways, e.g., large volumes of low concentrations of belinostat during one extended period of time or several times a day. The quantities can be administered for one or more consecutive days, intermittent days, or a combination thereof per week (7 day period). Alternatively, low volumes of high concentrations of belinostat may be administered during a short period of time, e.g., once a day for one or more days either consecutively, intermittently, or a combination thereof per week (7 day period). For example, a dose of 300 mg/m$^2$ per day can be administered for 5 consecutive days for a total of 1500 mg/m$^2$ per treatment. In another example, a dose of 250 mg/m$^2$ per day can be administered for 4 consecutive days for a total of 1000 mg/m$^2$ per treatment. In another dosing regimen, the number of consecutive days can also be 5, with treatment lasting for 2 or 3 consecutive weeks for a total of 3000 mg/m$^2$ and 4500 mg/m$^2$ total treatment.

Typically, an intravenous formulation can be prepared which contains a concentration of belinostat of between about 1.0 mg/mL to about 10 mg/mL, e.g. 2.0 mg/mL, 3.0 mg/mL, 4.0 mg/mL, 5.0 mg/mL, 6.0 mg/mL, 7.0 mg/mL, 8.0 mg/mL, 9.0 mg/mL and 10 mg/mL and administered in amounts to achieve the doses described above. In one example, a sufficient volume of intravenous formulation can be administered to a patient in a day such that the total dose for the day is between about 250 mg/m$^2$ and about 1500 mg/m². In a particular embodiment, the belinostat is administered intravenously to a patient at a rate of 900 mg/m² every 24 hours.

Similarly, pralatrexate can be administered to a patient in a number of suitable ways.

For example, one possible suitable dosing schedule may involve the administration of 30 mg/m² weekly×6 weeks followed by a one week rest.

In another particular embodiment, the patient can receive pralatrexate in quantities sufficient to deliver between about 7.5 mg/m² to 30 mg/m² per day.

As contemplated herein, intravenous formulations of pralatrexate can be prepared by one of skill in the art. Such formulations may contain, e.g., a concentration of pralatrexate of between about 1.0 mg/mL to about 30 mg/mL, e.g. 2.0 mg/mL, 3.0 mg/mL, 4.0 mg/mL, 5.0 mg/mL, 6.0 mg/mL, 7.0 mg/mL, 8.0 mg/mL, 9.0 mg/mL, 10 mg/mL, 20 mg/mL, and 30 mg/mL and administered in amounts to achieve the doses described above. In one example, a sufficient volume of intravenous formulation can be administered to a patient in a day such that the total dose for the day is between about 7.5 mg/m² and about 30 mg/m². In a particular embodiment, 30 mg/m² pralatrexate may be administered as an intravenous push over 3 to 5 minutes once weekly for 6 weeks in 7-week cycles.

As contemplated herein, based on data provided herein, appropriate dosage amounts of belinostat and pralatrexate for use in the methods of the instant invention may be determined by one of skill in the art. As contemplated herein, in particular embodiments, the dosage of pralatrexate may range from 7.5 mg/m² to 30 mg/m², and/or the dosage of belinostat may range from 250 mg/m² to 1000 mg/m², administered to a patient in any manner contemplated herein.

As contemplated herein, belinostat and pralatrexate may be administered to a patient according to the methods of the present invention sequentially in any order, simultaneously, or a combination thereof. For example, belinostat may be administered prior to the administration of pralatrexate (e.g., up to 7, 14, 21 days prior); administered after administration of pralatrexate (e.g., up to 7, 14, 21 days afterwards), administered at the same time as pralatrexate, or in a manner which is a combination of such dosing regimens.

For example, the combination therapy may be on a 21-day cycle wherein belinostat is administered every 24 hours for five days, then pralatrexate and belinostat are administered on days 2-5 and 10-13. In a specific embodiment, belinostat may be administered every 24 hours for 5 days every three weeks. In each cycle, the pralatrexate regimen will be administered on cycle day 3 after administration of belinostat.

Kits

In another aspect, the invention pertains to a kit or kit-of-parts comprising belinostat, e.g., as a component of a pharmaceutically acceptable formulation provided in a suitable container and/or with suitable packaging; and pralatrexate, e.g., as a component of a pharmaceutically acceptable formulation provided in a suitable container and/or with suitable packaging; and wherein said kit or kit-of-parts contains the indicated agents in dosage amounts suitable for use in a method for treating a B-cell or T-cell lymphoma according to the methods of the instant invention. As contemplated herein, physically discrete units suitable as unitary dosages for human subjects or other mammals, each unit containing a predetermined quantity of active ingredient calculated to produce the desired therapeutic effect when administered concomitantly or sequentially, and optionally in association with a suitable pharmaceutical excipient, may be included. Typical unit dosage forms may include, e.g., pre-measured ampoules or syringes of liquid compositions; or pills, tablets, capsules or the like in the case of solid compositions.

As contemplated herein, the kit or kit-of-parts may further comprise instructions, e.g., written instructions for use, for example, instructions for administration of a combination of belinostat and pralatrexate to a subject in need thereof. In one embodiment, the instructions include a list of indications (e.g., types of lymphoma) for which the indicated combination of active agents is a suitable treatment. In various embodiments, the kit or kit-of-parts further comprises appropriate reagents (e.g., buffers, solvents) and/or devices (e.g., tubes, syringes) to facilitate administration of the active agents.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. The disclosure will be further described in the following examples, which are intended to further illustrate certain embodiments of the invention and are not intended to limit the invention in any way.

EXAMPLES

Example 1

The growth inhibitory effects of belinostat alone, and in combination with pralatrexate, was assayed in several different human lymphoma cell lines in vitro. The endpoint for cell based studies was 72 hours after treatment; cell viability was measured using CellTiter-Glo® and combination effects determined using Chou-Talalay analysis with $IC_{50}$ and combination index values as provided herein. A possible sequence-dependent synergy or additive effects of belinostat along with pralatrexate in several human lymphoma cell lines was investigated.

Materials and Methods

Cell Lines: A panel of lymphoma cell lines (KARPAS-299 [Human Non-Hodgkin's Ki-positive Large Cell Lymphoma (T cell origin)], Jeko-1 [Mantle Cell Lymphoma (B cell origin)] and HUT-78 [Cutaneous T lymphocyte (T cell origin)] are cultured in RPMI (10% FBS), RPMI (20% FBS) and Iscove's media (20% FBS) respectively with penicillin and streptomycin (Mediatech, Inc). RPMI and Iscove's media used in this study contains folic acid (2.3 μm and 2 mg/500 ml), respectively.

Serum used in this study is un-dialyzed fetal bovine serum (Atlanta Biologics) and contains<1 nm of 5-methyltetrahydrofolate.

The cultures are maintained in T75-cm² culture flasks at 37° C., 95% air humidity, and 5% $CO_2$. The cells are subcultured at 80-90% confluence and are seeded into 96-well plates at $1.5 \times 10^4$ cells per well for each experiment.

Cell Treatment: Treatment is initiated 24 hours after plating. For single agent studies, cells are treated with increasing concentrations of belinostat and pralatrexate between 0.005-1 μM and 0.001 μM-0.2 Mm, respectively. For combination studies, cells are treated concurrently with belinostat plus pralatrexate for seventy-two hours at 37° C. at the following constant $IC_{50}$ ratios: 0.25×, 0.5×, 1×, 2× and 4×. After 72 hrs treatment, cell viability is determined using the CellTiter-Glo® Luminescent Cell Viability Assay (Promega).

Growth Inhibition Assay: Cell viability is determined using the CellTiter-Glo® Luminescent Cell Viability assay from Promega. The CellTiter-Glo® assay is a homogeneous method to determine and compare cell viability using ATP utilization. Following treatment, 100 µl of growth medium is removed and cells are incubated with 100 µl CellTiter-Glo® reagent for two minutes with nutation and incubated at room temperature for ten additional minutes to stabilize the luminescence signal; luminescence is then measured using a Biotek luminometer with values reported in (Lum).

Data analysis: Cell viability in each assay is expressed as a percentage versus untreated control cells. Viability $IC_{50}$ values are determined as the concentrations of the chemical agents causing 50% decrease in cell viability. The data are fitted into CalcuSyn software and single and combination effects are determined using Chou-Talalay analysis with $IC_{50}$ and Combination Index (CI) determined using Biosoft CalcuSyn software where C<1=Synergism, C=1=Additive; C>1=Antagonism (Ting-Chao Chou and P Talalay, "Quantitative analysis of dose-effect relationships: the combined effect of multiple drugs or inhibitors" Advan. Enzym. Regul. Vol. 22, pp 27-55, 1985).

Results

Data from the experiments is provided below in Tables 1-2, and is discussed below:

Belinostat: Single agent $IC_{50}$ values for belinostat (PXD101) after 72 hr exposure across a panel of lymphoma cell lines are 0.09-0.21 µM. Relative $IC_{50}$ values of 0.203 µM (KARPAS-299), 0.103 µM (Jeko-1), 0.097 µM (HUT-78) are utilized for combination experiments (Table 1).

Pralatrexate: Single agent $IC_{50}$ values for pralatrexate after 72 hr exposure across a panel of lymphoma cell lines are 0.002-0.025 µM. Relative $IC_{50}$ values of 0.024 µM (KARPAS-199), 0.0187 µM (Jeko-1), 0.0028 µM (HUT-78) are utilized for combination experiments (Table 1).

Belinostat+Pralatrexate: In combination studies, $IC_{50}$ values for belinostat (PXD101) are 0.127 µM (KARPAS-299), 0.087 µM (Jeko-1) and 0.17 µM (HUT-78). $IC_{50}$ values for pralatrexate are calculated as follows: 0.0036 µM (KARPAS-299), 0.0021 µM (Jeko-1), 0.0041 µM (HUT-78) and are utilized for the combination experiments.

In KARPAS-299, belinostat combination with pralatrexate shows synergistic effect at low $IC_{50}$ concentration and additive effect at 1×$IC_{50}$ concentration (CI=1) and antagonistic effect at higher $IC_{50}$ concentrations. Whereas in Jeko-1, 1×$IC_{50}$ and lower $IC_{50}$ show antagonism and higher $IC_{50}$ showed synergistic effects. In the case of HUT-78, 0.5× and 1×$IC_{50}$ show synergistic effect (CI<1) (Table 2).

Conclusion: Single agent belinostat treatment showed comparable $IC_{50}$ values ranging from 0.09 µM-0.21 µM in the assayed lymphoma cell lines. Likewise, pralatrexate treatment showed $IC_{50}$ values ranging from 0.002 µM-0.025 µM Table 1). Unexpectedly, in different lymphoma cell lines tested, including different B cell lines and T cell lines, the combination of belinostat and pralatrexate produced synergistic growth inhibitory effects at different $IC_{50}$ concentrations. Specifically, in vitro data demonstrate synergistic growth inhibitory effects are produced with the combination of belinostat and pralatrexate in KARPAS-299 cells at lower $IC_{50}$ combinations; in Jeko-1 it showed synergism at higher combinations and in HUT-78 cells, synergism was achieved at 1×$IC_{50}$ treatment (Table 2).

In Vitro Study Results:

TABLE 1

Single Agent IC50 Determination (µM)

| Drug | KARPAS-299 | Jeko-1 | HUT-78 |
|---|---|---|---|
| Belinostat | 0.203 | 0.103 | 0.097 |
| Pralatrexate | 0.024 | 0.0187 | 0.0028 |

TABLE 2

Combination Index (CI)

| KARPAS-299 | | | | |
|---|---|---|---|---|
| PDX-SA-KARPAS (µM) | Prala-SA-KARPAS (µM) | Fold | Fa | CI |
| 0.05 | 0.00625 | 0.25X | 0.24 | 0.47 |
| 0.1 | 0.0125 | 0.5X | 0.33 | 0.588 |
| 0.2 | 0.025 | 1X | 0.54 | 1.048 |
| 0.4 | 0.05 | 2X | 0.87 | 1.698 |
| 0.8 | 0.1 | 4X | 0.98 | 2.148 |
| Jeko-1 | | | | |
| PDX-SA-Jeko-1 (µM) | Prala-SA-Jeko-1 µM | Fold | Fa | CI |
| 0.025 | 0.005 | 0.25X | 0.095 | 66.054 |
| 0.05 | 0.01 | 0.5X | 0.23 | 49.073 |
| 0.1 | 0.02 | 1X | 0.33 | 2.281 |
| 0.2 | 0.04 | 2X | 0.86 | 0.858 |
| 0.4 | 0.08 | 4X | 0.98 | 0.574 |
| HUT-78 | | | | |
| PDX-SA-HUT-78 (µM) | Prala-SA-HUT-78(µM) | Fold | Fa | CI |
| 0.025 | 0.00075 | 0.25X | 0.001 | 1.437 |
| 0.05 | 0.0015 | 0.5X | 0.079 | 0.575 |
| 0.1 | 0.003 | 1X | 0.25 | 0.869 |
| 0.2 | 0.006 | 2X | 0.56 | 1.419 |
| 0.4 | 0.012 | 4X | 0.9 | 1.543 |

CI < 1 = Synergism;
C = 1 = Additive;
C > 1 = Antagonism
SA = Single agent;
Fa = Fraction affected;
CI = Combination Index The cell lines used in this study are derived from human patients and, therefore, the results obtained are relevant for in vivo use in humans. The studies described here show that the combination of belinostat and pralatrexate are synergistic when used in certain ratios. Thus, based on the studies described here, appropriate doses of the two agents can be tested in humans to determine synergistic doses for administration to patients in vivo.

Those skilled in the art will recognize, or be able to ascertain using no more than routine experimentation, many equivalents to the specific embodiments of the invention described herein. Such equivalents are intended to be encompassed by the following claims.

Thus, while the preferred embodiments of the invention have been illustrated and described, it is to be understood that this invention is capable of variation and modification, and should not be limited to the precise terms set forth. The inventors desire to avail themselves of such changes and alterations which may be made for adapting the invention to various usages and conditions. Such alterations and changes may include, for example, different pharmaceutical compositions for the administration of the agents according to the present invention to a mammal; different amounts of agent in the compositions to be administered; different times and means of administering the agents according to the present invention; and different materials contained in the administration dose including, for example, combinations of different agents, or combinations of the agents according to the present invention together with other biologically active compounds for the same, similar or differing purposes than the desired utility of those agents specifically disclosed herein. Such changes and alterations also are intended to include modifications of the specific desired agents described herein in which such changes alter the agent in a manner as not to change the desired potential of the agent, but as to change solubility of the agent in the pharmaceutical composition to be administered or in the body, absorption of the agent by the body, protection of the agent for either shelf life or within the body until such time as the biological action of the agent is able to bring about the desired effect, and such similar modifications. Accordingly, such changes and alterations are properly intended to be within the full range of equivalents, and therefore within the purview of the following claims.

The invention and the manner and process of making and using it have been thus described in such full, clear, concise and exact terms so as to enable any person skilled in the art to which it pertains, or with which it is most nearly connected, to make and use the same.

The invention claimed is:

1. A pharmaceutical composition, comprising:
   a first amount of belinostat;
   a second amount of pralatrexate; and
   a pharmaceutical carrier or excipient,
   wherein the first amount and the second amount comprise a therapeutically effective amount,
      wherein the therapeutically effective amount exhibits a synergistic growth inhibitory effect compared to the first amount alone or the second amount alone when used for the treatment of a mantle cell lymphoma, or a peripheral T-cell lymphoma, wherein the peripheral T-cell lymphoma is an anaplastic large cell lymphoma (ALCL) or a cutaneous T-cell lymphoma,
      wherein the therapeutically effective amount has a molar ratio of belinostat to pralatrexate of 8:1 when used for the treatment of the ALCL,
      wherein the therapeutically effective amount has a molar ratio of belinostat to pralatrexate of 5:1 when used for the treatment of the mantle cell lymphoma, and
      wherein the therapeutically effective amount has a molar ratio of belinostat to pralatrexate of 33:1 when used for the treatment of the cutaneous T-cell lymphoma.

2. The pharmaceutical composition of claim 1, wherein said composition further comprises a vitamin selected from the group consisting of vitamin B12 and folic acid.

3. The pharmaceutical composition of claim 1, wherein the first amount of belinostat is in a concentration ranging from about 1.0 mg/mL to about 10 mg/mL, and wherein the second amount of pralatrexate is in a concentration ranging from about 1.0 mg/mL to about 30 mg/mL.

4. The pharmaceutical composition of claim 1, wherein the pharmaceutical carrier or excipient is one or more selected from the group consisting of lactose, starch, sucrose, glucose, methyl cellulose, microcrystalline cellulose, sodium croscarmellose, magnesium stearate, dicalcium phosphate, calcium sulfate, mannitol, sorbitol, ethanol, glycerol, water, starch, gelatin, beta-lactose, acacia, tragacanth, sodium aliginate, carboxymethylcellulose, polyethylene glycol, sodium oleate, sodium stearate, magnesium stearate, sodium benzoate, sodium acetate, sodium chloride, agar, bentonite, xanthan gum, glucuronic acid, L-lactic acid, acetic acid, and citric acid.

5. The pharmaceutical composition of claim 1,
   wherein the therapeutically effective amount when used for the treatment of the ALCL is sufficient to deliver from $0.25 \times IC_{50}$ to $0.5 \times IC_{50}$ for each of belinostat and pralatrexate at a target site for the ALCL,
   wherein the therapeutically effective amount when used for the treatment of the mantle cell lymphoma is sufficient to deliver from $2 \times IC_{50}$ to $4 \times IC_{50}$ for each of belinostat and pralatrexate at a target site for the mantle cell lymphoma, and
   wherein the therapeutically effective amount when used for the treatment of the cutaneous T-cell lymphoma is sufficient to deliver from $0.5 \times IC_{50}$ to $1 \times IC_{50}$ for each of belinostat and pralatrexate at a target site for the cutaneous T-cell lymphoma.

* * * * *